(12) United States Patent
Park

(10) Patent No.: US 10,743,962 B2
(45) Date of Patent: Aug. 18, 2020

(54) ALL-IN-ONE CLEANER

(71) Applicant: MEGAGEN IMPLANT CO., LTD., Gyeongsan-si, Gyeongsangbuk-do (KR)

(72) Inventor: Kwang Bum Park, Daegu (KR)

(73) Assignee: MEGAGEN IMPLANT CO., LTD. (KR)

( * ) Notice: Subject to any disclaimer, the term of this patent is extended or adjusted under 35 U.S.C. 154(b) by 10 days.

(21) Appl. No.: 15/035,219

(22) PCT Filed: Nov. 4, 2014

(86) PCT No.: PCT/KR2014/010508
§ 371 (c)(1),
(2) Date: May 6, 2016

(87) PCT Pub. No.: WO2015/069002
PCT Pub. Date: May 14, 2015

(65) Prior Publication Data
US 2016/0270875 A1    Sep. 22, 2016

(30) Foreign Application Priority Data
Nov. 7, 2013  (KR) .......................... 10-2013-0135077

(51) Int. Cl.
*A61B 90/70* (2016.01)
*A61C 19/00* (2006.01)
(Continued)

(52) U.S. Cl.
CPC ............ *A61B 90/70* (2016.02); *A61C 19/002* (2013.01); *B08B 1/001* (2013.01); *B08B 3/08* (2013.01);
(Continued)

(58) Field of Classification Search
CPC ..................................... B08B 3/044; B08B 3/12; B08B 1/001; A61B 90/70; A61B 90/701; A61C 17/20; B24B 31/102
See application file for complete search history.

(56) References Cited

U.S. PATENT DOCUMENTS 3,166,064 A  *  1/1965  Waltman ................. F24C 15/10
                                                                 126/214 A
3,421,528 A  *  1/1969  Gomez ................ A61C 17/036
                                                                 134/188
(Continued)

FOREIGN PATENT DOCUMENTS

CN      101124000 A      2/2008
CN      201261017        6/2009
(Continued)

*Primary Examiner* — Michael E Barr
*Assistant Examiner* — Kevin G Lee
(74) *Attorney, Agent, or Firm* — Renaissance IP Law Group LLP

(57) ABSTRACT

An all-in-one cleaner is disclosed. An all-in-one cleaner, according to an embodiment of the present invention, comprises: a cleaner body; a soaking unit which is provided on one side of the cleaner body and carries out a soaking step on a subject to be cleaned; a washing unit which is provided near the soaking unit and carries out a washing step on the subject to be cleaned, for which the soaking step has been completed; and a rinsing unit which is provided near the washing unit and carries out a rinsing step on the subject to be cleaned, for which the washing step has been completed.

17 Claims, 9 Drawing Sheets

(51) Int. Cl.
*B24B 31/10* (2006.01)
*B08B 1/00* (2006.01)
*B08B 3/08* (2006.01)
*B08B 3/12* (2006.01)
*A61L 2/14* (2006.01)

(52) U.S. Cl.
CPC .............. *B08B 3/12* (2013.01); *B24B 31/102* (2013.01); *A61L 2/14* (2013.01)

(56) References Cited

U.S. PATENT DOCUMENTS

| | | | | |
|---|---|---|---|---|
| 5,022,858 | A * | 6/1991 | Castellini | A61C 19/002 433/77 |
| 5,093,079 | A | 3/1992 | Bakaitis et al. | |
| 5,494,531 | A * | 2/1996 | Azuma | A61C 19/002 134/102.3 |
| 5,662,516 | A * | 9/1997 | You | B24B 1/005 451/104 |
| 5,988,193 | A * | 11/1999 | Hernandez | A61C 19/002 134/184 |
| 6,176,609 | B1 * | 1/2001 | Cleveland | B01F 13/0818 366/273 |
| 6,357,907 | B1 * | 3/2002 | Cleveland | B01F 13/0818 366/273 |
| 6,528,015 | B1 * | 3/2003 | Lin | A61L 2/186 422/23 |
| 8,967,168 | B1 * | 3/2015 | Gusanders | A61B 1/121 134/184 |
| 2002/0159917 | A1 | 10/2002 | Swart et al. | |
| 2003/0029474 | A1 * | 2/2003 | Gibbs | A61C 19/002 134/1 |
| 2004/0037735 | A1 | 2/2004 | DePaula et al. | |
| 2009/0205687 | A1 * | 8/2009 | Onishi | B08B 9/032 134/136 |
| 2009/0308416 | A1 * | 12/2009 | Utz | B08B 3/12 134/115 R |
| 2010/0269852 | A1 * | 10/2010 | Palfy | A61C 17/036 134/1 |
| 2013/0273816 | A1 * | 10/2013 | Kan | B24B 49/00 451/11 |

FOREIGN PATENT DOCUMENTS

| | | |
|---|---|---|
| EP | 0646363 A1 | 4/1995 |
| JP | 2011251062 A | 12/2011 |
| KR | 101116042 B1 | 2/2012 |
| KR | 20120047699 | 5/2012 |
| KR | 101270570 | 6/2013 |

* cited by examiner

ALL-IN-ONE CLEANER

TECHNICAL FIELD

The present inventive concept relates to an all-in-one cleaner, and more particularly, to all-in-one cleaner which may improve an efficiency of cleaning a subject to be cleaned by sequentially performing a soaking process, a washing process, and a rinsing process with respect to the subject to be cleaned by using a single piece of equipment.

BACKGROUND ART

Although cleaners are used for a variety of purpose in a variety of fields, in the following description, cleaners used for medical purposes are described.

After surgical operations or treatments, blood or living body tissues may adhere on medical tools such as scalpels or other medical instruments, as various subjects to be cleaned.

Since infectious pathogenic bacteria are highly likely to be latent on the medical instruments, the medical tools are necessarily cleaned before reusing the medical tools in order to prevent secondary infection by the infectious pathogenic bacteria.

The cleaning of the medical tools is not limited to the surgical operations only. For example, in dental clinics, various medical tools used for various dental treatments including implant treatments are necessarily cleaned so as to prevent secondary infection by infectious pathogenic bacteria.

Accordingly, hospitals including dental clinics are equipped with all-in-one cleaners to clean medical tools used for operations and treatments.

However, for all-in-one cleaners currently used in hospitals, like general cleaners for cleaning general articles such as typical noble metals, artificial tooth, glasses, etc., medical tools to be cleaned are dipped into cleaning water and cleaned merely by, for example, ultrasonic waves, so that it is difficult to substantially provide a perfect washing effect with respect to the medial tools.

For example, although it is expected to provide a substantially perfect cleaning effect only when a soaking process, a washing process, and a rinsing process are performed on medical tools, no all-in-one cleaner capable of providing all functions as above has been provided up to date and thus research and development on such an all-in-one cleaner is quite demanding.

DETAILED DESCRIPTION OF THE INVENTIVE CONCEPT

Technical Problem

The present inventive concept provides an all-in-one cleaner which may improve an efficiency of cleaning a subject to be cleaned by sequentially performing a soaking process, a washing process, and a rinsing process with respect to the subject to be cleaned by using a single piece of equipment.

Advantageous Effects

According to the exemplary embodiments of the present inventive concept, there is provided an all-in-one cleaner which may improve an efficiency of cleaning a subject to be cleaned by sequentially performing a soaking process, a washing process, and a rinsing process with respect to the subject to be cleaned by using a single piece of equipment

BEST MODE

Figure 1:
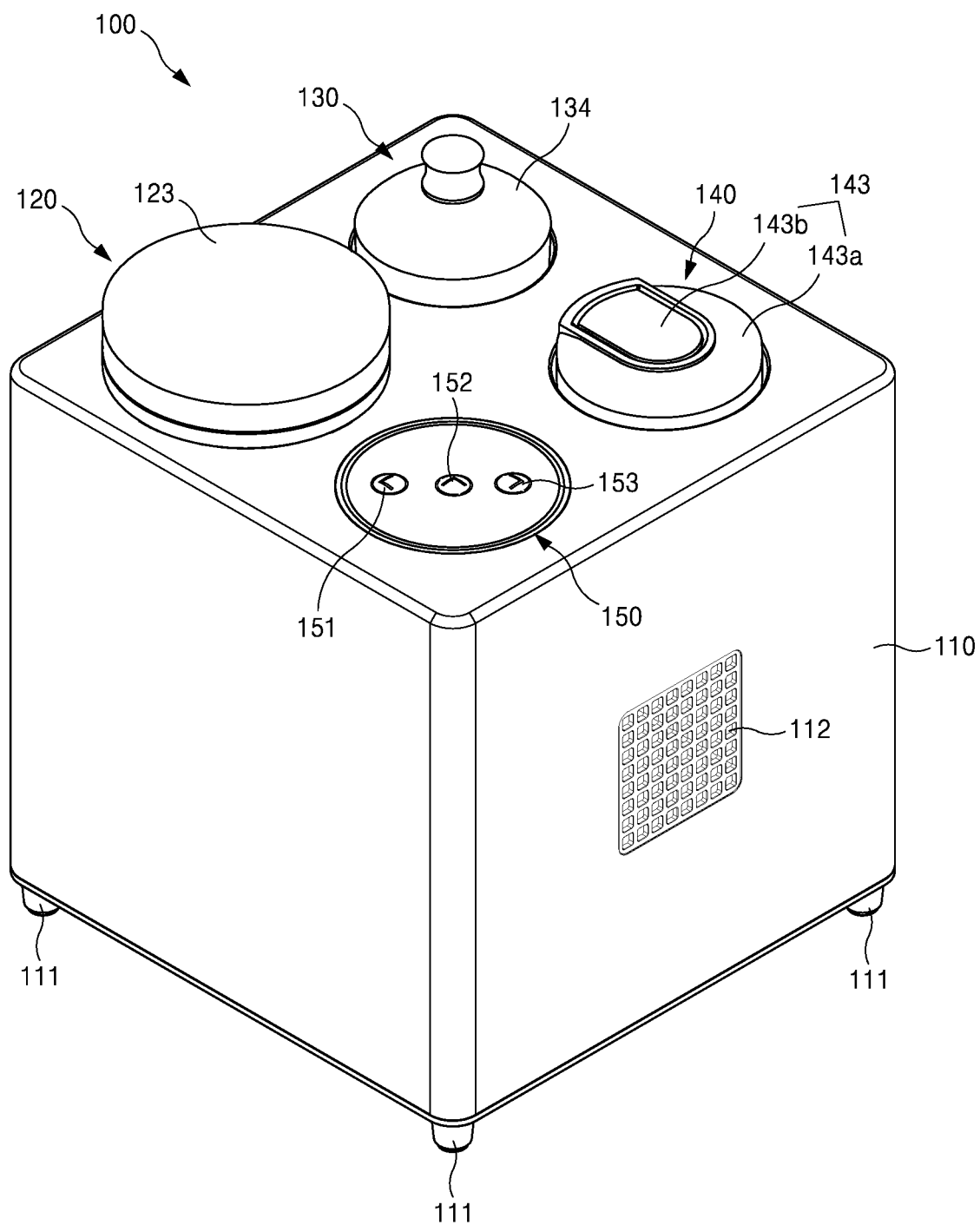
FIG. 1 is a perspective view of an all-in-one cleaner according to an embodiment.

According to an aspect of the present inventive concept, an all-in-one cleaner includes a cleaner body, a soaking unit provided at one side of the cleaner body and performing a soaking process with respect to a subject to be cleaned, a washing unit arranged around the soaking unit and performing a washing process with respect to the subject to be cleaned, for which the soaking process has been completed, and a rinsing unit arranged around the washing unit and performing a rinsing process with respect to the subject to be cleaned, for which the washing process has been completed.

The all-in-one cleaner may further include an input panel provided on the cleaner body and comprising a plurality of input buttons to provide an input signal for operations of the soaking unit, the washing unit, and the rinsing unit.

The all-in-one cleaner may further include a controller controlling the operations of the soaking unit, the washing unit, and the rinsing unit in response to an input signal of the input button.

The soaking unit, the washing unit, the rinsing unit, and the input panel may be arranged adjacent to one another on an upper surface of the cleaner body.

The soaking unit may be an ultrasonic soaking unit that soaks the subject to be cleaned in an ultrasonic cleaning method.

The ultrasonic soaking unit may include an ultrasonic soaking jar detachably coupled to a soaking part groove, which is formed to be inwardly sunken from an upper surface of the cleaner body, and filled with liquid to soak the subject to be cleaned, and an ultrasonic wave generation module provided inside the cleaner body in an area of the soaking part groove and generating ultrasonic waves with respect to the liquid in the ultrasonic soaking jar.

Ultrasonic soaking jar connectors may be respectively provided on a bottom portion of the soaking part groove and a lower portion of the ultrasonic soaking jar.

The ultrasonic soaking unit may further include an ultrasonic soaking jar lid for opening or closing a top opening of the ultrasonic soaking jar.

The washing unit may be a barrel washing unit that washes the subject to be cleaned by using a plurality of washing pins that are rotated.

The barrel washing unit may include a barrel washing jar detachably coupled to a washing part groove, which is formed to be inwardly sunken from an upper surface of the cleaner body, and is filled with liquid to wash the subject to be cleaned, for which the soaking process has been completed, and a washing pin rotation driving module provided inside the cleaner body in an area of the washing part groove and rotating the plurality of washing pins in the barrel washing jar.

The washing pin rotation driving module may be a magnetic washing pin rotation driving module that rotates the plurality of washing pins in the barrel washing jar by using a magnetic force.

The barrel washing unit may further include a barrel washing jar lid for opening or closing a top opening of the barrel washing jar.

The rinsing unit may be a sterilized rinsing unit that rinses the subject to be cleaned by a plasma ion sterilization method.

The sterilized rinsing unit may include a sterilized rinsing jar detachably coupled to a rinsing part groove, which is formed to be inwardly sunken from the upper surface of the cleaner body 110, and is filled with liquid to rinse the subject to be cleaned, for which the washing process has been completed, and a plasma ion generation module provided inside the cleaner body in an area of the rinsing part groove and generating plasma ions with respect to the liquid in the sterilized rinsing jar.

Sterilized rinsing jar connectors may be respectively provided on a bottom portion of the rinsing part groove and a lower portion of the sterilized rinsing jar.

The sterilized rinsing unit may further include a sterilized rinsing jar lid for opening or closing a top opening of the sterilized rinsing jar.

The sterilized rinsing jar lid may include an outer fixed lid portion, and an inner rotating lid portion arranged in the outer fixed lid portion and opening and closing an inside of the outer fixed lid portion by being rotated.

The subject to be cleaned may be a medical tool used in a dental clinic.

MODE OF THE INVENTION

The attached drawings for illustrating preferred embodiments of the present inventive concept are referred to in order to gain a sufficient understanding of the present inventive concept, the merits thereof, and the objectives accomplished by the implementation of the present inventive concept.

Hereinafter, the present inventive concept will be described in detail by explaining preferred embodiments of the inventive concept with reference to the attached drawings. Like reference numerals in the drawings denote like elements.

Figure 2:
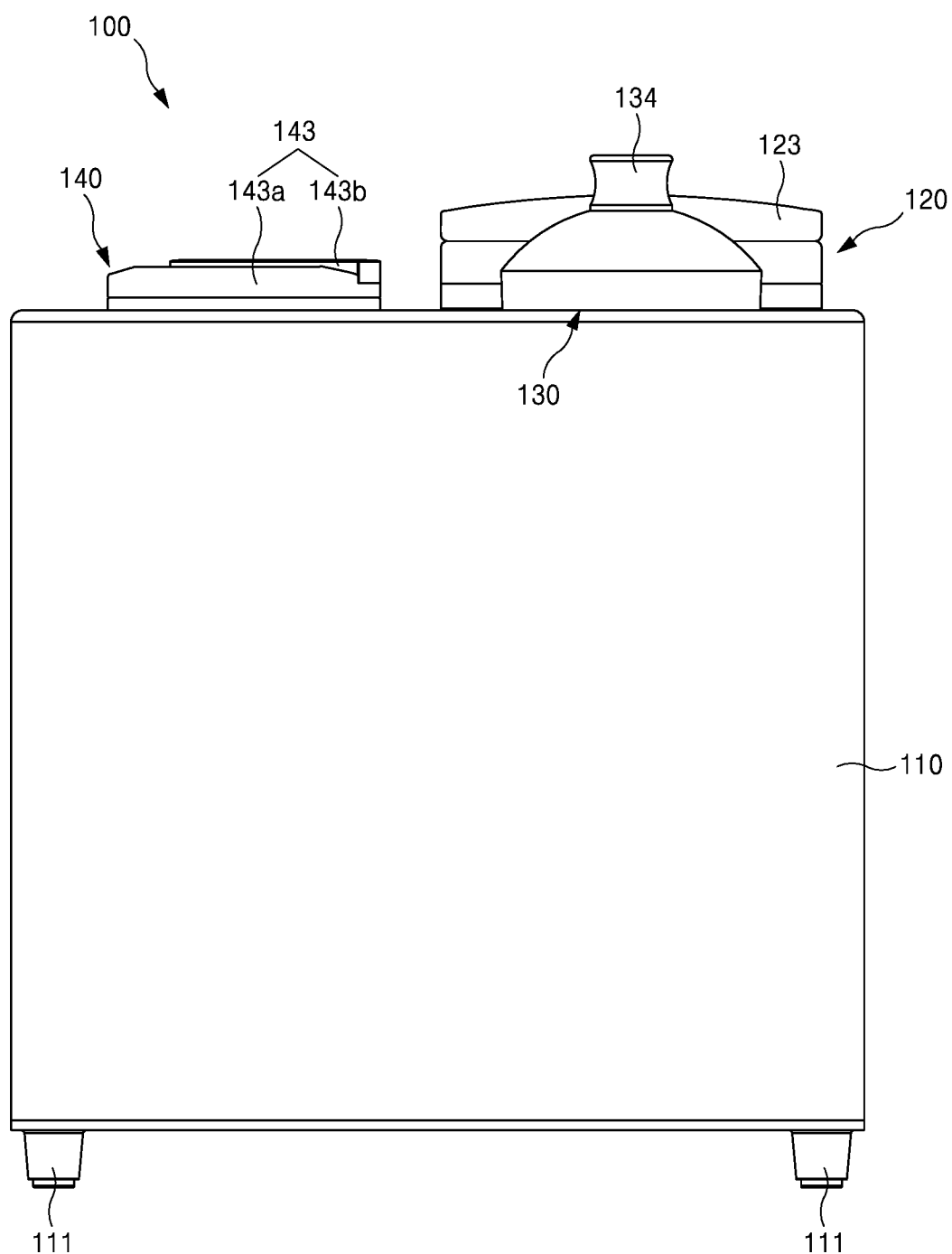
FIG. 2 is a side view of FIG. 1.
Figure 3:
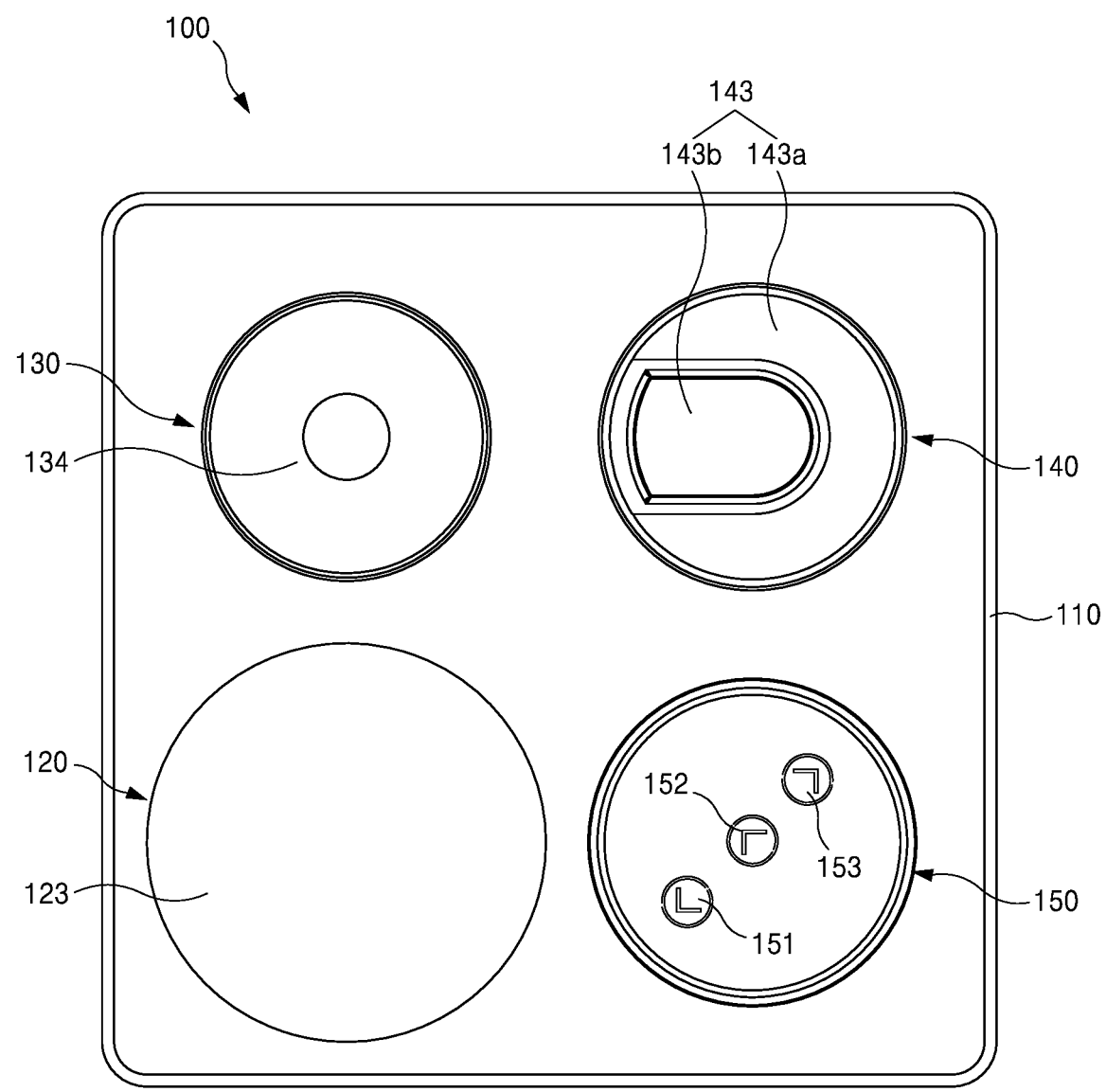
FIG. 3 is a plan view of FIG. 1.
Figure 4:
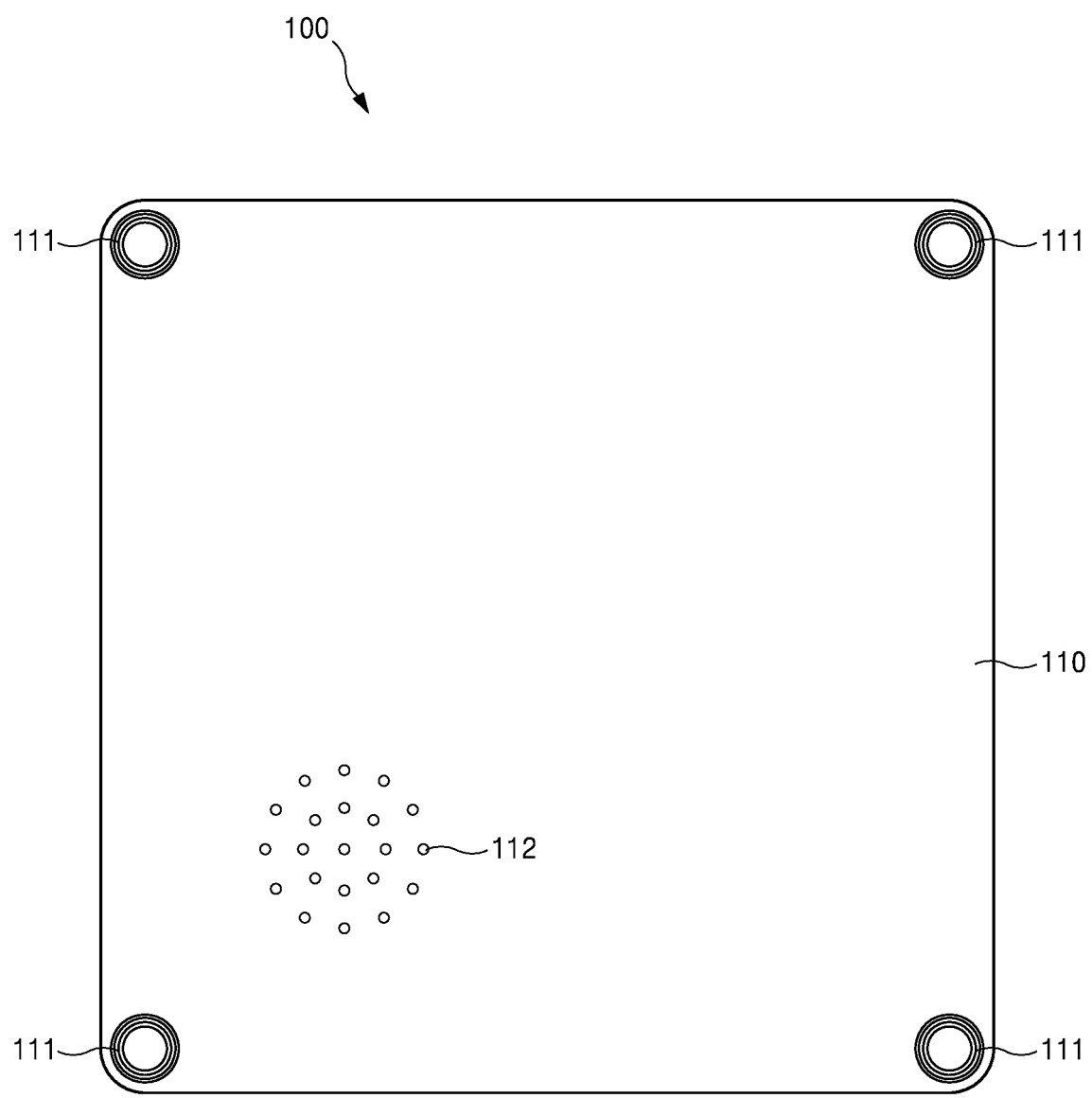
FIG. 4 is a rear view of FIG. 1.
Figure 5:
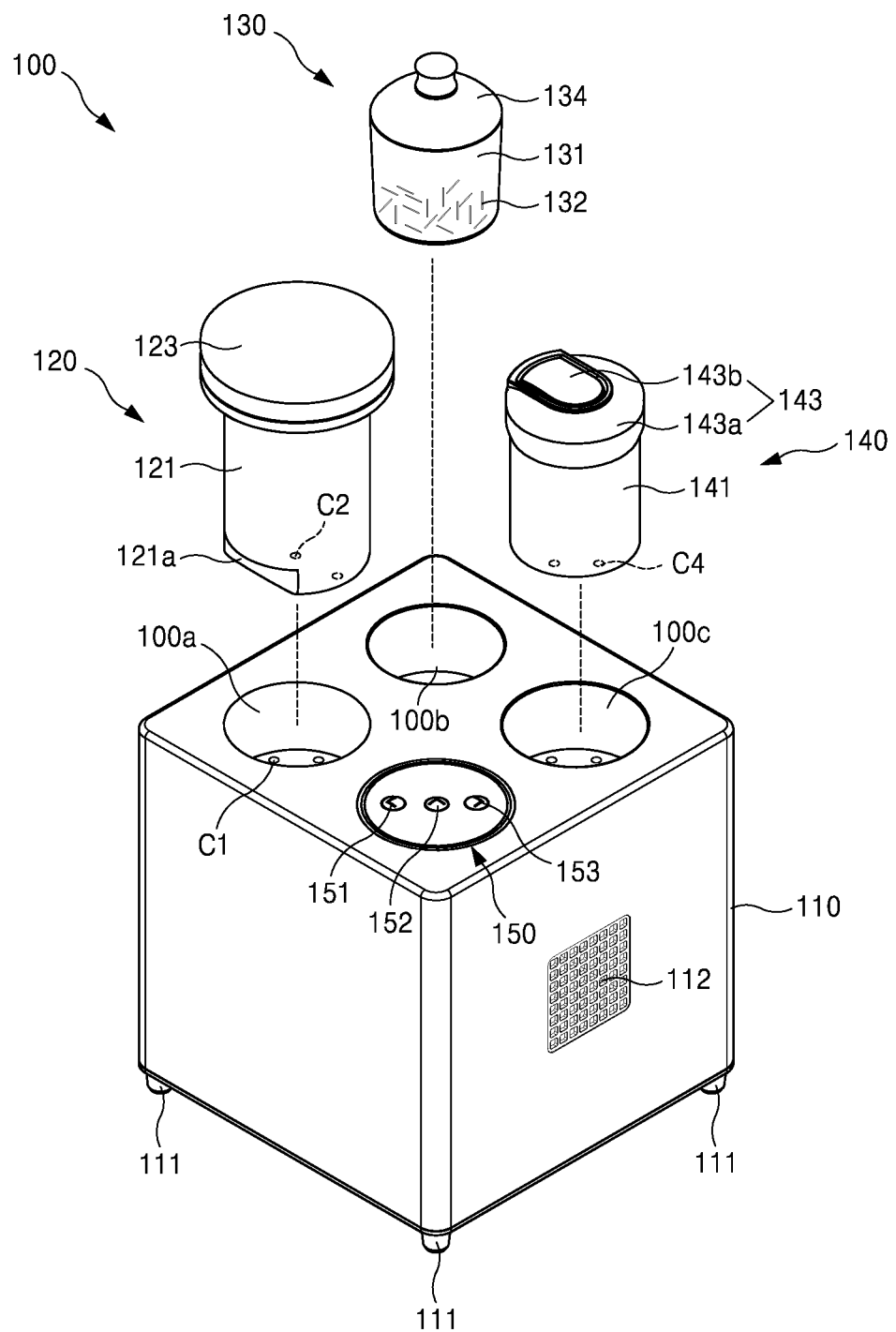
FIG. 5 is an exploded perspective view of FIG. 1.
Figure 6:
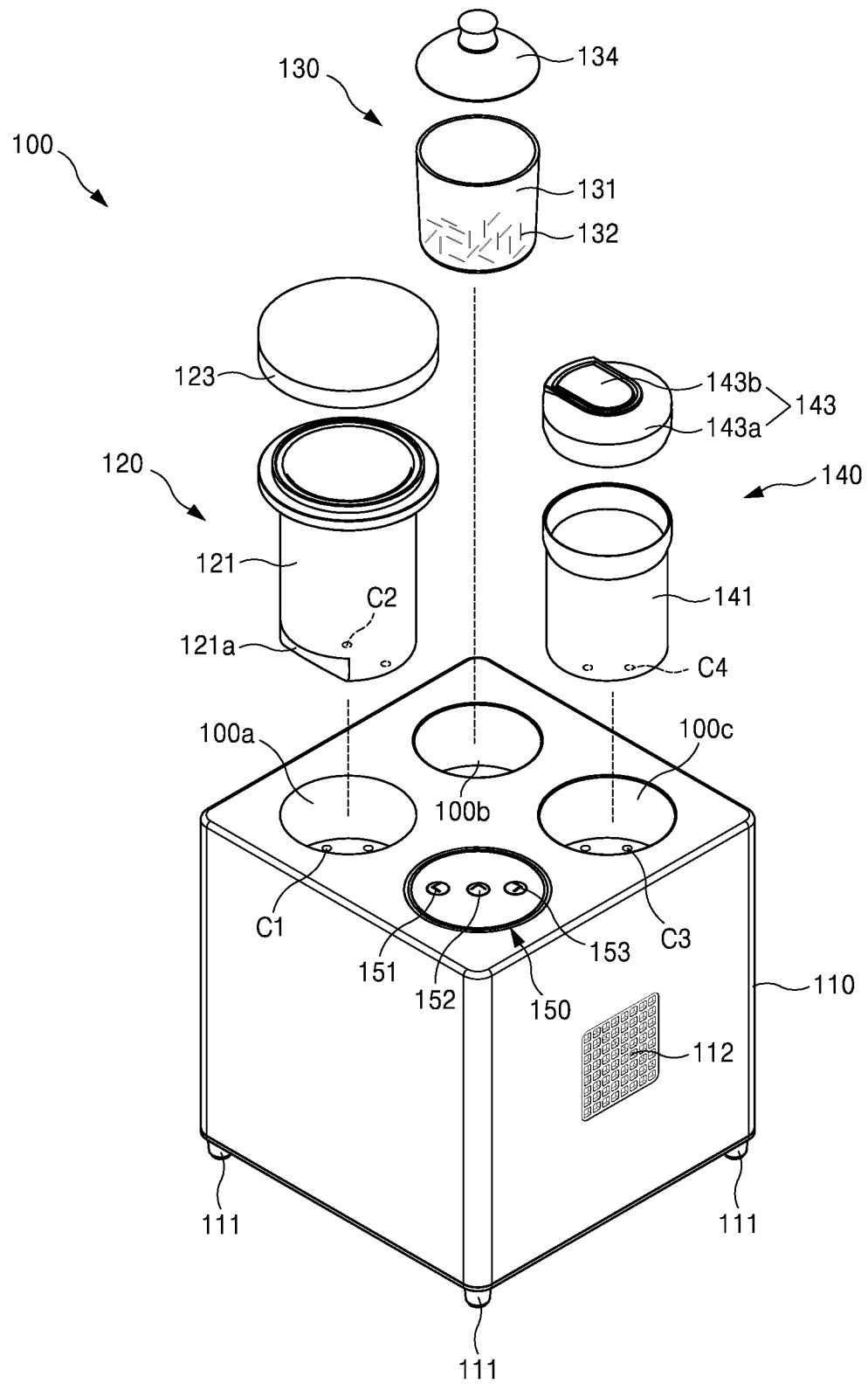
FIG. 6 is a partial exploded view of FIG. 5.
Figure 7:
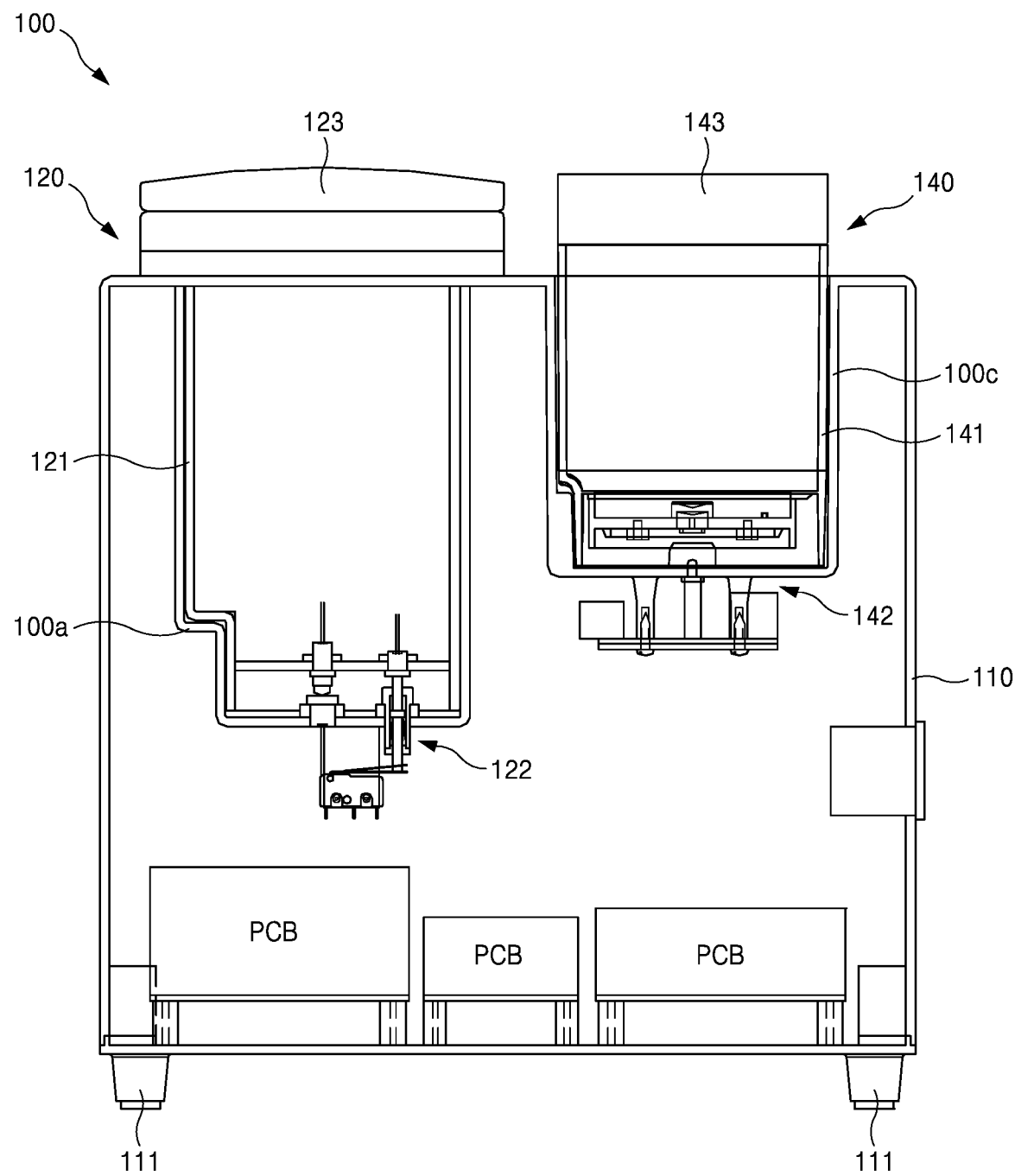
FIG. 7 is a cross-sectional structural view of an all-in-one cleaner, showing structures of a soaking unit and a rinsing unit.
Figure 8:
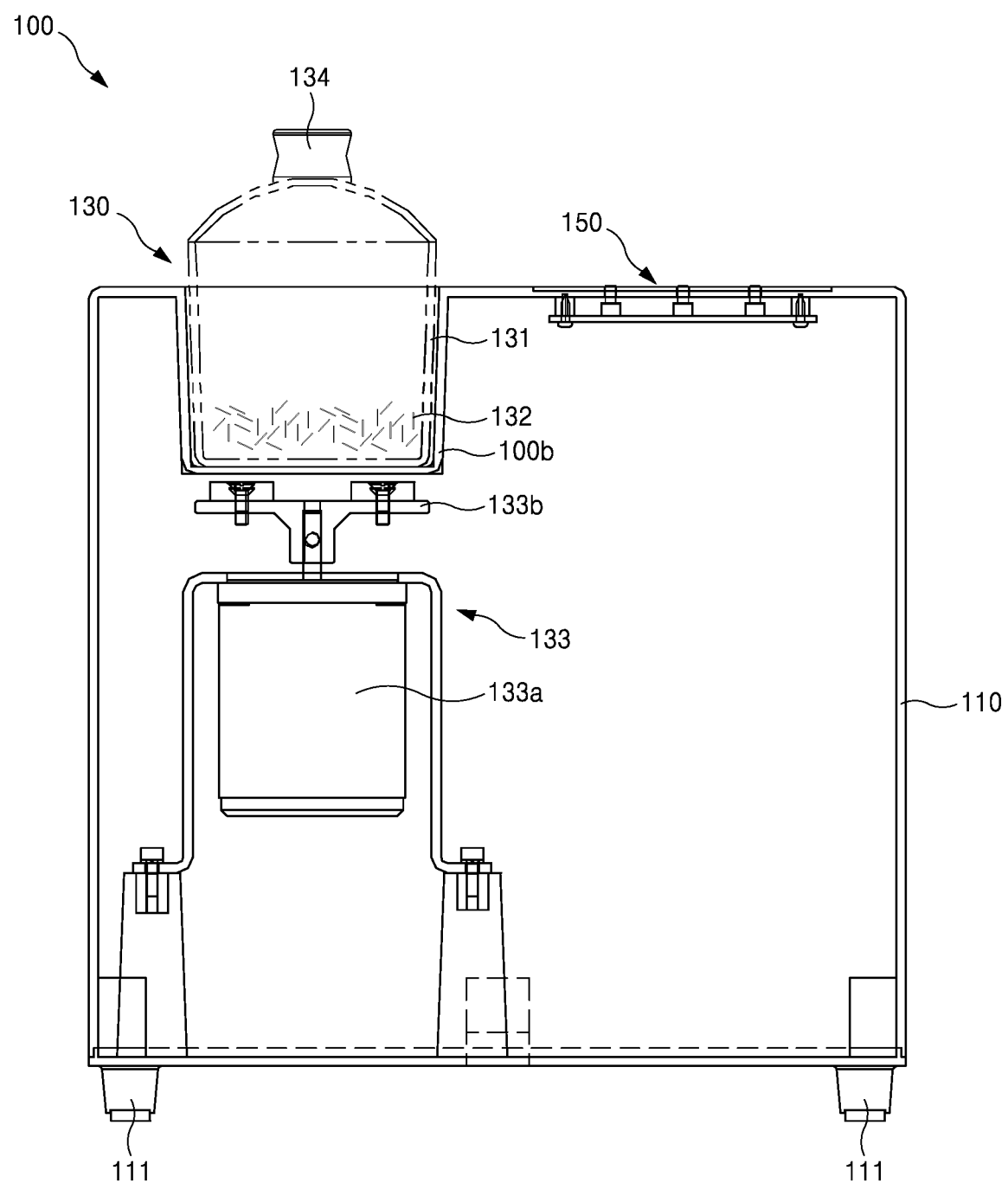
FIG. 8 is a cross-sectional structural view of an all-in-one cleaner, showing structures of a washing unit.
Figure 9:
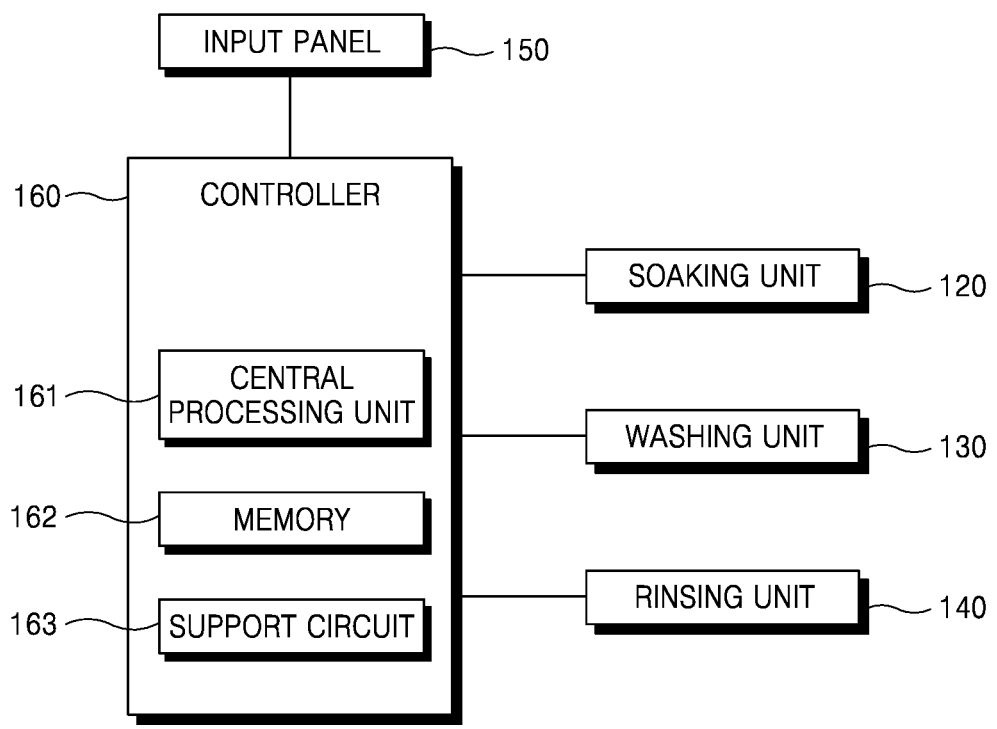
FIG. 9 is a control block diagram of an all-in-one cleaner, according to an embodiment.

FIG. 1 is a perspective view of an all-in-one cleaner according to an embodiment. FIG. 2 is a side view of FIG. 1. FIG. 3 is a plan view of FIG. 1. FIG. 4 is a rear view of FIG. 1. FIG. 5 is an exploded perspective view of FIG. 1. FIG. 6 is a partial exploded view of FIG. 5. FIG. 7 is a cross-sectional structural view of an all-in-one cleaner, showing structures of a soaking unit and a rinsing unit. FIG. 8 is a cross-sectional structural view of an all-in-one cleaner, showing structures of a washing unit. FIG. 9 is a control block diagram of an all-in-one cleaner, according to an embodiment.

Referring to the above drawings, an all-in-one cleaner 100 according to the present embodiment may improve an efficiency of cleaning a subject to be cleaned by sequentially performing a soaking process, a washing process, and a rinsing process with respect to the subject to be cleaned by using a single piece of equipment. The al-in-one cleaner 100 may include a cleaner body 110, a soaking unit 120, a washing unit 130, a rinsing unit 140, an input panel 150, and a controller 160.

For reference, although the all-in-one cleaner 100 according to the present embodiment may be used for various purposes in various fields, the following description focuses on the all-in-one cleaner 100 that is used for medical purposes.

Accordingly, a subject to be cleaned may be medical instruments or scalpels for surgical operations, various medical tools used for implant treatments in dental clinics, or additional articles such as artificial tooth. In the following description, all the above articles may be referred to a subject to be cleaned without discrimination.

Elements that constitute the all-in-one cleaner 100 are described below in detail.

First, the cleaner body 110 form an external appearance of the all-in-one cleaner 100 according to the present embodiment. The soaking unit 120, the washing unit 130, the rinsing unit 140, the input panel 150, and the controller 160 may be supported by the cleaner body 110.

In the present embodiment, although the cleaner body 110 has a shape of a rectangular container, the cleaner body 110 may have various shapes, for example, a shape of a circular container. Accordingly, the right scope of the present inventive concept is not limited to the shape illustrated on the drawings.

A plurality of feet 111 are provided at a bottom side of the cleaner body 110. The feet 111 may be manufactured of a rubber material and may support the all-in-one cleaner 100 according to the present embodiment on a support surface at a certain position without slipping.

Although the feet 111 are illustrated to be block structures made of a rubber material on the drawings, some of the feet 111 may be wheels. When some of the feet 111 are wheels, it is advantageous that the all-in-one cleaner 100 according to the present embodiment may be easily moved to another position.

A plurality of ventilation holes 112 may be formed in a lateral surface of the cleaner body 110. Since heat inside the cleaner body 110 may be discharged to the outside through the ventilation holes 112 formed in the lateral surface of the cleaner body 110, damage to parts due to overheat may be prevented.

A plurality of drain holes 113 are formed in a bottom surface of the cleaner body 110 as illustrated in FIG. 4. Water that intrudes into the cleaner body 110 may be easily discharged out of the cleaner body 110 through the drain holes 113 formed in the bottom surface of the cleaner body 110.

A plurality of printed circuit boards (PCBs) for operations of the soaking unit 120, the washing unit 130, and the rinsing unit 140 are arranged in a bottom area in the cleaner body 110, as illustrated in FIG. 7. While one of the PCBs may be a main PCB, the other PCBs may be individual PCBs for individually controlling the operations of the soaking unit 120, the washing unit 130, and the rinsing unit 140. However, the above structure may be changed without limitation and thus a detailed description thereof is omitted.

In the structure of the cleaner body 110, the soaking unit 120, the washing unit 130, the rinsing unit 140, and the input panel 150 are arranged adjacent to one another on an upper surface of the cleaner body 110.

Accordingly, a user, without bending forward or without moving and using the input panel 150, may allow the subject to be cleaned to sequentially move among the soaking unit 120, the washing unit 130, and the rinsing unit 140 to carry out a soaking process, a washing process, and a rinsing process, thereby having a cleaning job performed very conveniently. As such, in the all-in-one cleaner 100 according to the present embodiment, the soaking process, the washing process, and the rinsing process may be sequentially performed on the subject to be cleaned in a single piece of equipment so that efficiency of cleaning of the subject to be cleaned may be much improved.

Next, the soaking unit 120 is provided at one side of the cleaner body 110 and performs a soaking process on the subject to be cleaned.

In the present embodiment, the soaking unit 120 may be the ultrasonic soaking unit 120 that soaks and cleans the subject to be cleaned in an ultrasonic wave cleaning method.

Although it is ideal to use the ultrasonic soaking unit 120 as the soaking unit 120, the present disclosure is not limited thereto and any other method, even if it is not the ultrasonic method, may belong to the right scope of the present inventive concept.

In the present embodiment, the ultrasonic soaking unit 120 may include an ultrasonic soaking jar 121 that is detachably coupled to a soaking part groove 110a, which is formed to be inwardly sunken from the upper surface of the cleaner body 110, and is filled with liquid to soak the subject to be cleaned, and an ultrasonic wave generation module 122 that is provided inside the cleaner body 110 in an area of the soaking part groove 110a and generates ultrasonic waves with respect to the liquid in the ultrasonic soaking jar 121.

The ultrasonic soaking jar 121 may have a shape of a cylindrical container with an open top portion. An ultrasonic soaking jar lid 123 is provided on a top opening of the ultrasonic soaking jar 121 to shield the top opening during operation.

A cut portion 121a is formed at one side of a lower end portion of the ultrasonic soaking jar 121. The cut portion 121a is provided only for the structure and may not be essentially formed.

Ultrasonic soaking jar connectors C1 and C2 are respectively provided on a bottom portion of the soaking part groove 110a and a lower portion of the ultrasonic soaking jar 121.

Since the ultrasonic soaking jar connectors C1 and C2 are respectively provided on the bottom portion of the soaking part groove 110a and the lower portion of the ultrasonic soaking jar 121, separate wires are not necessary unlike existing equipment. Also, since the ultrasonic soaking unit 120 are operated only when the ultrasonic soaking jar connectors C1 and C2 contact each other, unnecessary power consumption may be reduced and the structure of the all-in-one cleaner 100 may be simplified.

The ultrasonic wave generation module 122 is provided inside the cleaner body 110 in the area of the soaking part groove 110a, as illustrated in FIG. 7, and generates ultrasonic waves with respect to the liquid in the ultrasonic soaking jar 121.

Ultrasonic cleaning is briefly described. When ultrasonic waves are generated in the liquid, a cavitation phenomenon that fine bubbles of high pressure and high temperature repeats generation and termination within a very short time occurs together and, as agitation effect and thermal operation of the ultrasonic waves cause synergism so that the subject to be cleaned may be cleaned deep inside, which is not seen, within a short time.

Also, when cavitation occurs in water that is liquid, chemical reactions of high temperature and high pressure are generated as follows.

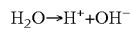

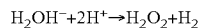

Hydrogen peroxide generated by the chemical reactions is a strong oxidizer that oxidizes other materials so that organic materials or microorganisms adhering on a surface of the subject to be cleaned are oxidized, thereby achieving cleaning and sterilization.

Since the ultrasonic cleaning is available when there is liquid, that is, water, the ultrasonic cleaning is a quick, safe, economic, and eco-friendly cleaning method, compared to any other existing cleaning methods. Tepid water may be used during cleaning, but the present disclosure is not limited thereto.

Next, the washing unit 130 is arranged around the soaking unit 120 and performs a washing process with respect to the subject to be cleaned, for which the soaking process has been completed.

In the present embodiment, the washing unit 130 may be a barrel washing unit 130 that washes the subject to be cleaned by using a plurality of washing pins 132 that are rotated.

For reference, the barrel washing refers to a method which produces a strong cleaning and polishing effect with respect to the subject to be cleaned by rotating the washing pins 132 by using a magnetic force.

Although it is ideal to use the barrel washing unit 130 as the washing unit 130, the present disclosure is not limited thereto and any other method, even if it is not the barrel washing method, may belong to the right scope of the present inventive concept.

In the present embodiment, the barrel washing unit 130 may include a barrel washing jar 131 that is detachably coupled to a washing part groove 110b, which is formed to be inwardly sunken from the upper surface of the cleaner body 110, and is filled with liquid to wash the subject to be cleaned, for which the soaking process has been completed, and a washing pin rotation driving module 133 that is provided inside the cleaner body 110 in an area of the washing part groove 110b and rotate the washing pins 132 in the barrel washing jar 131.

The barrel washing jar 131 has a shape of a cylindrical container with an open top portion. A barrel washing jar lid 134 is provided on a top opening of the barrel washing jar 131 to cover the top opening during operation.

The washing pin rotation driving module 133 is provided inside the cleaner body 110 in the area of the washing part groove 110b, and rotates the washing pins 132 in the barrel washing jar 131.

In the present embodiment, the washing pin rotation driving module 133 is the magnetic washing pin rotation driving module 133 that rotates the washing pins 132 in the barrel washing jar 131 by using a magnetic force.

In the magnetic washing pin rotation driving module 133, as illustrated in FIG. 8, as the washing pins 132 in the barrel washing jar 131 are strongly rotated by a motor 133a and a magnet rotating disc 133b rotated by the motor 133a, a washing job may be performed.

Next, the rinsing unit 140 is arranged around the washing unit 130 and performs a rinsing process on the subject to be cleaned, for which the washing process has been completed.

In the present embodiment, the rinsing unit 140 may be the sterilized rinsing unit 140 that rinses the subject to be cleaned in a plasma ion sterilization method.

Although it is ideal to use the sterilized rinsing unit 140 as the rinsing unit 140, the present disclosure is not limited thereto and any other method, even if it is not the Barrel Washing method, may belong to the right scope of the present inventive concept.

In the present embodiment, the sterilized rinsing unit 140 may include a sterilized rinsing jar 141 that is detachably coupled to a rinsing part groove 110*c*, which is formed to be inwardly sunken from the upper surface of the cleaner body 110, and is filled with liquid to rinse the subject to be cleaned, for which the washing process has been completed, and a plasma ion generation module 142 that is provided inside the cleaner body 110 in an area of the rinsing part groove 110*c* and generates plasma ions with respect to the liquid in the sterilized rinsing jar 141.

Sterilized rinsing jar connectors C3 and C4 are respectively provided on a bottom portion of the rinsing part groove 110*c* and a lower portion of the sterilized rinsing jar 141.

Since the sterilized rinsing jar connectors C3 and C4 are respectively provided on the bottom portion of the rinsing part groove 110*c* and the lower portion of the sterilized rinsing jar 141, separate wires are not necessary unlike existing equipment. Also, since the sterilized rinsing unit 140 are operated only when the sterilized rinsing jar connectors C1 and C2 contact each other, unnecessary power consumption may be reduced and the structure of the all-in-one cleaner 100 may be simplified.

The sterilized rinsing jar 141 may have a shape of a cylindrical container with an open top portion. A sterilized rinsing jar lid 143 is provided on a top opening of the sterilized rinsing jar 141 to cover the top opening during operation.

In the present embodiment, the sterilized rinsing jar lid 143 may include an outer fixed lid portion 143*a* and an inner rotating lid portion 143*b* arranged in the outer fixed lid portion 143*a* and opening and closing the inside of the outer fixed lid portion 143*a* by being rotated.

As such, when the sterilized rinsing jar lid 143 is manufactured with the outer fixed lid portion 143*a* and the inner rotating lid portion 143*b*, thin and long members such as toothbrushes may be sterilized and rinsed by rotating the inner rotating lid portion 143*b* only, without opening the outer fixed lid portion 143*a*.

The plasma ion generation module 142 is provided inside the cleaner body 110 in the area of the rinsing part groove 110*c*, as described above, and generates plasma ions with respect to the liquid in the sterilized rinsing jar 141.

In other words, during the sterilized rinsing process, for example, daily life water such as general tap water or underground water may be used. In this state, the plasma ion generation module 142 generates low-temperature plasma in water to convert the water to strongly sterilized water with hydroxyl radicals, thereby performing a sterilized operation. Accordingly, the rinsing process in which not only simple rinsing but also sterilization is performed may be hygienic.

Next, the input panel 150 is provided in an upper surface area of the cleaner body 110 and provides an input signal for the operations of the soaking unit 120, the washing unit 130, and the rinsing unit 140.

A plurality of input buttons 151-153 to individually select the operations of the soaking unit 120, the washing unit 130, and the rinsing unit 140 are provided in the input panel 150.

Finally, the controller 160 controls the operations of the soaking unit 120, the washing unit 130, and the rinsing unit 140 in response to input signals of the input buttons 151-153.

The controller 160 performing the above functions may include a central processing unit (CPU) 161, a memory 162, and a support circuit 163, as illustrated in FIG. 9.

The central processing unit 161 may be one of various industrially applicable computer processors for controlling the operations of the soaking unit 120, the washing unit 130, and the rinsing unit 140 in response to the input signals of the input buttons 151-153 in the all-in-one cleaner 100 according to the present embodiment.

The memory 162 is connected to the central processing unit 161. The memory 162, which is a computer-readable recording medium, may be installed at a local or remote place, and may be at least one easily usable memory, for example, random access memory (RAM), read-only memory (ROM), floppy discs, hard disks, or any digital storage medium.

The support circuit 163 is coupled to the central processing unit 161 and supports a typical operation of a processor. The support circuit 163 may include cache, a power supply, a clock circuit, an input/output circuit, a sub-system, etc.

In the all-in-one cleaner 100 according to the present embodiment, the controller 160 controls the operations of the soaking unit 120, the washing unit 130, and the rinsing unit 140, in response to the input signals of the input buttons 151-153. In this state, a series of processes of the controller 160 controlling the operations of the soaking unit 120, the washing unit 130, and the rinsing unit 140, in response to the input signals of the input buttons 151-153 may be stored in the memory 162. Typically, a software routine may be stored in the memory 162. The software routine may be stored or executed by another central processing unit (not shown).

Although the process according to the present inventive concept is described to be executed by software routines, at least part of the processes of the present inventive concept may be executed by hardware. As such, the processes of the present inventive concept may be implemented by software executed on a computer system, hardware such as integrated circuits, or a combination of software and hardware.

A method of using the all-in-one cleaner 100 according to the present embodiment is described below.

First, a power plug is connected and a power button is turned on.

Then, after the ultrasonic soaking jar 121 is filled about ⅔ with tepid ware, for example, a subject to be cleaned is placed in the ultrasonic soaking jar 121.

Then, an ultrasonic soaking washing process is performed by pressing the first input button 151 to operate the ultrasonic wave generation module 122. The ultrasonic soaking washing process may be performed for about 20 minutes. However, the operation time may be freely changed and thus the right scope of the present inventive concept is not limited by the above figure.

When the ultrasonic soaking washing process is completed, the subject to be cleaned, for which the ultrasonic soaking washing process has been completed, is taken out of the ultrasonic soaking jar 121 and then put into the barrel washing jar 131.

Then, the second input button 152 is pushed to operate the washing pin rotation driving module 133 and thus the washing pins 132 are strongly rotated, thereby performing a barrel washing process.

The barrel washing process may be performed for about 20 minutes. However, the operation time may be freely changed and thus the right scope of the present inventive concept is not limited by the above figure.

When the barrel washing process is completed, the subject to be cleaned, for which the barrel washing process has been completed, is taken out of the barrel washing jar 131 and then put into the sterilized rinsing jar 141.

Then, the third input button 153 is pushed to operate the plasma ion generation module 142 and thus a sterilized rinsing process is performed.

The sterilized rinsing process may be performed for about 5 minutes. However, the operation time may be freely changed and thus the right scope of the present inventive concept is not limited by the above figure. When the sterilized rinsing is completed, the subject to be cleaned is taken out of the sterilized rinsing jar 141.

In the all-in-one cleaner according to the present inventive concept having the above structure and operation, an efficiency of cleaning a subject to be cleaned may be improved by sequentially performing a soaking process, a washing process, and a rinsing process with respect to the subject to be cleaned by using a single piece of equipment.

While this inventive concept has been particularly shown and described with reference to preferred embodiments thereof, it will be understood by those of ordinary skill in the art that various changes in form and details may be made therein without departing from the spirit and scope of the inventive concept as defined by the appended claims. Therefore, the scope of the inventive concept is defined not by the detailed description of the inventive concept but by the appended claims, and all differences within the scope will be construed as being included in the present inventive concept.

INDUSTRIAL APPLICABILITY

The present inventive concept may be used for a medical field including dentistry.

The invention claimed is:

1. An all-in-one cleaner comprising:
   a cleaner body having an upper surface, a soaking part groove formed to be inwardly sunken within the upper surface at one side of the cleaner body;
   a soaking unit for performing a soaking process with respect to a subject to be cleaned, wherein the soaking unit includes a soaking jar detachably coupled to the soaking part groove;
   a washing unit arranged around the soaking unit for performing a washing process with respect to the subject to be cleaned, for which the soaking process has been completed;
   a rinsing unit arranged around the washing unit for performing a rinsing process with respect to the subject to be cleaned, for which the washing process has been completed; and
   a washing part groove and a rinsing part groove, each inwardly sunken within the upper surface of the cleaner body,
   wherein the washing unit is detachably coupled to the washing part groove,
   wherein the rinsing unit is detachably coupled to the rinsing part groove,
   wherein the soaking unit, washing unit and rinsing unit are simultaneously accessible to a user from the upper surface of the cleaner body,
   wherein a bottom of the soaking jar is closed so as to retain a liquid therein when the soaking jar is detached from its respective groove,
   wherein the soaking unit, the washing unit, and the rinsing unit, are arranged adjacent to one another on an upper surface of the cleaner body;
   wherein the washing unit is a barrel washing unit for washing the subject to be cleaned by using a plurality of washing pins that are rotatable, and wherein the plurality of washing pins are directly exposed to an interior of a barrel washing jar; and
   wherein the barrel washing unit comprises:
      the barrel washing jar detachably coupled to a washing part groove, which is formed to be inwardly sunken from an upper surface of the cleaner body, and is capable of being filled with liquid to wash the subject to be cleaned, for which the soaking process has been completed, wherein the plurality of washing pins are located in the barrel washing jar; and
      a washing pin rotation driving module provided inside the cleaner body in an area of the washing part groove for rotating the plurality of washing pins in the barrel washing jar.

2. The all-in-one cleaner of claim 1, wherein the soaking unit is an ultrasonic soaking unit for soaking the subject to be cleaned in an ultrasonic cleaning method.

3. The all-in-one cleaner of claim 2, wherein the soaking jar is an ultrasonic soaking jar, wherein the ultrasonic soaking jar is capable of being filled with liquid to soak the subject to be cleaned; and wherein the ultrasonic soaking unit further includes an ultrasonic wave generation module provided inside the cleaner body in an area of the soaking part groove and for generating ultrasonic waves with respect to the liquid in the ultrasonic soaking jar.

4. The all-in-one cleaner of claim 3, wherein ultrasonic soaking jar connectors are respectively provided at a bottom surface of the soaking part groove and a lower surface of the ultrasonic soaking jar.

5. The all-in-one cleaner of claim 3, wherein the ultrasonic soaking unit further comprises an ultrasonic soaking jar lid for opening or closing a top opening of the ultrasonic soaking jar.

6. The all-in-one cleaner of claim 1, wherein the washing pin rotation driving module is a magnetic washing pin rotation driving module for rotating the plurality of washing pins in the barrel washing jar by using a magnetic force.

7. The all-in-one cleaner of claim 1, wherein the barrel washing unit further comprises a barrel washing jar lid for opening or closing a top opening of the barrel washing jar.

8. The all-in-one cleaner of claim 1, wherein the rinsing unit is a sterilized rinsing unit for rinsing the subject to be cleaned by a plasma ion sterilization method.

9. The all-in-one cleaner of claim 8, wherein the sterilized rinsing unit comprises:
   a sterilized rinsing jar detachably coupled to a rinsing part groove, which is formed to be inwardly sunken from the upper surface of the cleaner body, and is capable of being filled with liquid to rinse the subject to be cleaned, for which the washing process has been completed; and
   a plasma ion generation module provided inside the cleaner body in an area of the rinsing part groove for generating plasma ions with respect to the liquid in the sterilized rinsing jar.

10. The all-in-one cleaner of claim 9, wherein sterilized rinsing jar connectors are respectively provided on a bottom portion of the rinsing part groove and a lower portion of the sterilized rinsing jar.

11. The all-in-one cleaner of claim 9, wherein the sterilized rinsing unit further comprises a sterilized rinsing jar lid for opening or closing a top opening of the sterilized rinsing jar.

12. The all-in-one cleaner of claim 11, wherein the sterilized rinsing jar lid comprises:

an outer fixed lid portion; and an inner rotating lid portion arranged in the outer fixed lid portion for opening and closing an inside of the outer fixed lid portion upon being rotated.

13. The all-in-one cleaner of claim 9, wherein a bottom of the sterilized rinsing jar is closed so as to retain a liquid therein when the sterilized rinsing jar is detached from its respective groove.

14. The all-in-one cleaner of claim 1, wherein the subject to be cleaned is a medical tool used in a dental clinic.

15. The all-in-one cleaner of claim 1, further comprising an panel provided on the cleaner body and comprising a plurality of input buttons to provide an input signal for operations of the soaking unit, the washing unit, and the rinsing unit.

16. The all-in-one cleaner of claim 15, further comprising a controller for controlling the operations of the soaking unit, the washing unit, and the rinsing unit in response to an input signal of the input button.

17. The all-in-one cleaner of claim 1, wherein a bottom of the barrel washing jar is closed so as to retain a liquid therein when the barrel washing jar is detached from its respective groove.

* * * * *